(12) United States Patent
Gacoin et al.

(10) Patent No.: US 11,401,463 B2
(45) Date of Patent: *Aug. 2, 2022

(54) LUMINESCENT PARTICLES BASED ON RARE EARTH ELEMENTS AND USE THEREOF AS A DIAGNOSTIC AGENT

(71) Applicants: ECOLE POLYTECHNIQUE, Palaiseau (FR); CENTRE NATIONAL DE LA RECHERCHE SCIENTIFIQUE, Paris (FR)

(72) Inventors: Thierry Gacoin, Bures-sur-Yvette (FR); Maximilian Richly, Paris (FR); Pascal Preira, Savigny-sur-Orge (FR); Antigoni Alexandrou, Palaiseau (FR); Cédric Bouzigues, Paris (FR); Rabei Mohammedi, Gif-sur-Yvette (FR)

(73) Assignees: ECOLE POLYTECHNIQUE, Palaiseau (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 333 days.

This patent is subject to a terminal disclaimer.

(21) Appl. No.: 16/614,055

(22) PCT Filed: May 18, 2018

(86) PCT No.: PCT/EP2018/063196
§ 371 (c)(1),
(2) Date: Nov. 15, 2019

(87) PCT Pub. No.: WO2018/211109
PCT Pub. Date: Nov. 22, 2018

(65) Prior Publication Data
US 2020/0172800 A1   Jun. 4, 2020

(30) Foreign Application Priority Data
May 18, 2017  (FR) ...................................... 1754416

(51) Int. Cl.
| | | |
|---|---|---|
| *C09K 11/02* | (2006.01) | |
| *C09K 11/77* | (2006.01) | |
| *G01N 33/543* | (2006.01) | |
| *A61K 33/02* | (2006.01) | |
| *A61K 49/10* | (2006.01) | |
| *C01F 1/00* | (2006.01) | |
| *A61K 49/00* | (2006.01) | |

(52) U.S. Cl.
CPC ............ *C09K 11/025* (2013.01); *A61K 33/02* (2013.01); *A61K 49/0065* (2013.01); *A61K 49/101* (2013.01); *C01F 1/00* (2013.01); *C09K 11/7794* (2013.01); *G01N 33/54346* (2013.01); *C01P 2006/40* (2013.01); *G01N 2458/40* (2013.01)

(58) Field of Classification Search
CPC .. C09K 11/025; C09K 11/7794; A61K 33/02; A61K 49/0065; A61K 49/101; C01F 1/00; G01N 33/54346; G01N 2458/40; C01P 2006/40
See application file for complete search history.

(56) References Cited

U.S. PATENT DOCUMENTS

2012/0058505 A1*  3/2012  Helms ...................... B82Y 5/00
                                                        435/29

FOREIGN PATENT DOCUMENTS

WO   2016079069 A1   5/2016

OTHER PUBLICATIONS

Iso et al., Langmuir 2014, 30, 1465-1471, (Year: 2014).*
Domitille Giaume et al. "Functionalized Luminescent Oxide Nanoparticles as Biological Probes" Mrs Proceedings vol. 942, Jan. 1, 2006.
Juan Want et al. "CTAB-assisted hydrothermal syntheseis of YVO: Eu powders in a wide pH range" Solid State Sciences, Elsevier, Paris, FR, vol. 14, No. 1, Oct. 21, 2011, pp. 191-196.
A. Huignard et al. "Synthesis and Luminescence Properties of ColloidalYVO4:Eu Phosphors" Chem. Mater. 12, 1090-1094; Mar. 29, 2000.
A. Huignard et al. "Synthesis and Characterizations of YVO4:Eu Colloids" Chem. Mater. 14, 2264-2269; Mar. 30, 2002.
G. Li et al "Hydrothermal Synthesis and Characterization of YVO4 and YVO4:Eu3+ Nanobelts and Polyhedral Micron Crystals" J. Phys. Chem. C 2008, 112, 6228-6231; Mar. 29, 2008.

(Continued)

*Primary Examiner* — Robert S Cabral
(74) *Attorney, Agent, or Firm* — Maschoff Brennan (57) ABSTRACT

The present invention concerns a luminescent particle comprising a nanoparticle of formula $$A_{1-x}Ln_xVO_{4(1-y)}(PO_4)_y \qquad (I)$$

in which A is selected from yttrium (Y), gadolinium (Gd), lanthanum (La), and mixtures thereof; Ln is selected from europium (Eu), dysprosium (Dy), samarium (Sm), neodymium (Nd), erbium (Er), ytterbium (Yb), and mixtures thereof; $0<x<1$; and $0\leq y<1$; characterized in that the nanoparticle on its surface has tetraalkylammonium cations in an amount such that said nanoparticle has a zeta potential, $\zeta$, of less than or equal to $-28$ mV in an aqueous medium with a pH$\geq$5, more particularly with a pH$\geq$5.5, and with an ionic conductivity $>100$ $\mu$S·cm$^{-1}$.

It also concerns a method for preparing such luminescent particles, a colloidal suspension of these particles, and the use thereof as a diagnostic agent, and also a diagnostic kit comprising such luminescent particles.

26 Claims, 4 Drawing Sheets

(56) References Cited

OTHER PUBLICATIONS

Yanjie Liang et al. "Hydrothermal synthesis and upconversion luminescent properties of YVO4:Yb3+,Er3+ nanoparticles" Journal of Alloys and Compounds 552 (2013) 289-293.

Genevie've Mialon et al. "High Temperature Strategy for Oxide Nanoparticle Synthesis" American Chemical Society; vol. 2, No. 12, 2505-2512, 2008.

Jwa-Min Nam et al. "Nanoparticle-Based Bio-Bar Codes for the Ultrasensitive Detection of Proteins" Sep. 26, 2003; Science vol. 301, pp. 1884-1886; www.sciencemag.org.

K. Riwotzki et al. "Wet-Chemical Synthesis of Doped Colloidal Nanoparticles: YVO4:Ln (Ln ) Eu, Sm, Dy)" J. Phys. Chem. B 1998, 102, 10129-10135.

Satoru Takeshita et al. "Low-temperature wet chemical synthesis and photoluminescence properties of YVO4: Bi3+, Eu3+ nanophosphors" Journal of Luminescence 128 (Mar. 2008) 1515-1522.

Hao Wu et al. "Size- and shape-tailored hydrothermal synthesis of YVO4 crystals in ultra-wide pH range conditions" J. Mater. Chem., 2003, 13, 1223-1228.

Zhenhe Xu et al. "Ln3þ (Ln = Eu, Dy, Sm, and Er) Ion-Doped YVO4 Nano/Microcrystals with Multiform Morphologies: Hydrothermal Synthesis, Growing Mechanism, and Luminescent Properties" Inorg. Chem. 2010, 49, 6706-6715; DOI: 10.1021/ic100953m.

Xingcai Wu et al. "Morphological Control and Luminescent Properties of YVO4:Eu Nanocrystals" J. Phys. Chem. B 2006, 110, 15791-15796.

Olaf Lehmann et al. "Synthesis of Eu3+-Doped Core and Core/Shell Nanoparticles and Direct Spectroscopic Identification of Dopant Sites at the Surface and in the Interior of the Particles" J. Am. Chem. Soc. 2004, 126, 45, 14935-14942.

K. Riwotzk et al. "Colloidal YVO4:Eu and YP0.95V0.05O4:Eu Nanoparticles: Luminescence and Energy Transfer Processes" J. Phys. Chem. B 2001, 105, 51, 12709-12713.

K. Riwotzk et al. "Liquid-Phase Synthesis of Doped Nanoparticles: Colloids of Luminescing LaPO4:Eu and CePO4:Tb Particles with a Narrow Particle Size Distribution" J. Phys. Chem. B 2000, 104, 13, 2824-2828.

Domitille Giaume et al. "Organic Functionalization of Luminescent Oxide Nanoparticles toward Their Application As Biological Probes" Langmuir 2008, 24, 19, 11018-11026.

K. Riwotzk et al. "Liquid-Phase Synthesis of Colloids and Redispersible Powders of Strongly Luminescing LaPO4:Ce, Tb Nanocrystals" Angew Chem Int Ed Engl. Feb. 2, 2001;40(3):573-576.

* cited by examiner

LUMINESCENT PARTICLES BASED ON RARE EARTH ELEMENTS AND USE THEREOF AS A DIAGNOSTIC AGENT

The present invention concerns the field of probes for detecting and/or quantifying substances of interest in biological samples. Its subject matter more particularly are novel luminescent inorganic particles, a process for preparing them, and use thereof for detecting and/or measuring the presence of proteins, antibodies, DNA, RNA, and other compounds in a biological sample.

The detection and/or quantification of concentrations of biomarkers, antibodies or DNA and RNA in biological samples (blood, serum, saliva, urine, cerebrospinal fluid, etc.) is indispensable for medical diagnosis.

In the field of in vitro or ex vivo diagnostics, medical analysis, and bioanalysis, a number of techniques have been proposed for detecting and/or measuring the presence of specific substances.

These techniques rely, generally speaking, on the use of a probe which is employed for detecting and/or quantifying a concentration in solution. These probes are coupled to molecules, DNA or proteins, which, directly or via a series of reactions, attach to the molecular species to be analyzed. Subsequently, the probes which have reacted can be detected by means of one or more techniques based, for example, on their luminescence, their absorption, their chemical reactivity, their radioactivity, etc.

The most commonly employed biochemical assays are enzyme-linked immunosorbent assays (ELISAs), which rely generally on the use of the enzyme horseradish peroxidase to bring about a reaction with a substrate and to quantify the chemical reaction which has occurred by measuring the absorption of the reaction product in the solution. The selection of the molecular compound to which the probe is coupled is critical to the efficacy of these probes. More specifically, the efficacy of these techniques is dependent on the specific affinity of the compound with the target substance. As examples, the publications referenced [1] and [2] detail the characteristics of these mechanisms.

Luminescent probes lead generally to more sensitive detection than the probes which are detected by their absorption, because, in the first case, the measurements of luminous intensity are made against a dark background, whereas, in the second case, the measurement is of a variation in luminous intensity (measurements against a light background). The luminescent probes currently available exhibit a number of disadvantages which prevent full exploitation of their potential as diagnostic probes. These drawbacks include, for example, the phenomenon of photobleaching in the case of organic fluorophores, this being manifested, after irreversible structural modifications, in the disappearance of the fluorescence, or else the phenomenon of emission flickering for semiconductor nanocrystals, or "quantum dots", when the probes undergo periodic cessation of emission and are consequently unsuited to producing a constant signal. Other drawbacks result, for example, from the width of the emission spectrum of the luminescent probes. Too wide an emission spectrum in fact makes it difficult to filter out the background signal which may be present, and affects the quality of this signal and, more particularly, affects the signal-to-noise ratio. Other factors to be borne in mind, in addition to the optical factors which contribute to the efficacy of the probe in a biological test, are the practical nature and the ease of use of the probe. There are certain particles, as in the case of semiconductor nanocrystals, which lose their luminescence characteristics after freezing, this representing a drawback for the storage of the bioconjugate agents. The ease of coupling of the probes to the molecular compound, which allows the desired molecules to be targeted, is also an aspect to be taken into account when choosing the appropriate probe. There are in fact a number of particles, including semiconductor nanocrystals, which are synthesized in organic solvents. Consequently, their use for biological applications requires additional steps of preparation of the surface in order to produce a dispersion of these particles in water, a process which may be very complicated to implement and may lack stability over time.

Furthermore, the colloidal properties of the particles/probes are critical to the conduct of the biological assays. Solutions with high colloidal stability are in fact capable of providing media for assays of high homogeneity, and consequently a better reproducibility in terms of the results of these assays.

Lastly, the complexity and the cost are important aspects in the selection of probes for diagnosis. For example, nanoparticles of gold, and their properties in terms of surface plasmon resonance, have been proposed as diagnostic probes, but have not become established as probes for in vitro diagnosis, possibly because of the complexity of the detection method [3], or perhaps a high cost. The semiconductor crystals for their part are synthesized in organic solvents and require procedures for dispersion in an aqueous medium, thereby making them complicated and hence costly to synthesize. Their functionalization with chemical groups allowing them to be coupled to the molecular compounds for recognition of the target molecules is reliant, moreover, on weak chemical bonds, thus limiting their stability, which is detrimental to the reproducibility of detection tests.

In this regard, nanoparticles doped with rare earth ions, such as $YVO_4$:Eu nanoparticles, prove particularly advantageous for use as probes for the detection/quantification of biomolecules.

Nanoparticles based on yttrium vanadate doped with rare earth elements, for example, have been described in detail by Riwotzki et al. [4] and Huignard et al. [5].

These nanoparticles are particularly advantageous for their excellent photostability, which allows a constant and prolonged signal to be acquired, and the absence of the phenomenon of emission flickering. Moreover, they have a narrow emission spectrum and a large Stokes shift of the emission. These two characteristics permit effective filtering of the emission signal of the nanoparticles, freeing it from interfering signals, to provide excellent signal-to-noise ratios. These nanoparticles also contain several tens of thousands of excitable ions which are responsible for the luminescence. Increasing the excitation intensity thus induces a linear increase in the luminosity of the particles, saturation of the emission being reached only for impracticable intensities.

Lastly, these nanoparticles do not lose their luminescence after freezing.

Synthesis of luminescent nanoparticles, doped with rare earth ions, in an organic solvent medium has been proposed, for example, in document EP 1 232 226 or in publications [6], [7] and [8].

The synthesis of these luminescent nanoparticles in an aqueous medium has also already been proposed, as for example by dropwise addition of solutions of yttrium and europium nitrates to an orthovanadate solution ($Na_3VO_4$) ([9], [10], [11], [12] and [13]).

Furthermore, publications [14]-[19] propose techniques for hydrothermal synthesis of $YVO_4$ nanoparticles doped with rare earth ions, employing ammonium metavanate, or orthovanadate, as a precursor.

Another document which may be cited is U.S. Pat. No. 8,337,804, which proposes a technique for preparing nanoparticles based on orthovanadate ions $VO_4^{3-}$, for example $YVO_4$:Eu, by employing a reaction medium containing water and at least one polyol.

Document EP 1 282 824 describes the use of surface-modified inorganic luminescent nanoparticles as probes for detecting a biological substance or other organic substance.

The luminescent nanoparticles obtained by the known synthesis pathways referred to above, and employed in an aqueous medium, are subject, however, to flocculation phenomena, and do not result in stable colloidal suspensions. Consequently, the quantity of nanoparticles in suspension is unstable over time and cannot be determined with precision.

This uncertainty in terms of the amount of luminescent particles in the colloidal suspensions employed is highly detrimental when they are used as probes in diagnostic techniques, since it affects the reproducibility of the results obtained, in the detection/quantification, for example, of the concentrations of biomolecules in the sample tested.

The luminescent particles doped with rare earth ions and obtained by the techniques of the prior art therefore do not provide complete satisfaction for use as diagnostic probes.

The present invention is specifically directed to proposing new luminescent particles and a new pathway for their synthesis that allow the aforesaid drawbacks to be overcome.

The invention more particularly proposes a means of accessing luminescent nanoparticles which exhibit enhanced colloidal stability in an aqueous medium, advantageously with a more reproducible synthesis and more reproducible subsequent steps of functionalization and of coupling to a molecular targeting agent.

According to a first aspect thereof, therefore, the invention provides a luminescent particle comprising a nanoparticle of formula:

$$A_{1-x}Ln_xVO_{4(1-y)}(PO_4)_y \quad (I)$$

in which:
A is selected from yttrium (Y), gadolinium (Gd), lanthanum (La), and mixtures thereof;
Ln is selected from europium (Eu), dysprosium (Dy), samarium (Sm), neodymium (Nd), erbium (Er), ytterbium (Yb), and mixtures thereof;
0<x<1, more particularly 0.2≤x≤0.6 and very particularly x being 0.4; and
0≤y<1;

characterized in that the nanoparticle has, at the surface, tetraalkylammonium cations.

According to another aspect thereof, the invention provides a method for preparing such particles, employing a coprecipitation reaction in aqueous medium starting from precursors of the elements A and Ln and in the presence of orthovanadate ions ($VO_4^{3-}$) and optionally phosphate ions ($PO_4^{3-}$), said reaction being performed in the presence of an effective amount of tetraalkylammonium cations.

More particularly, the amount of tetraalkylammonium cations is such that said nanoparticle has a zeta potential, ζ, in aqueous medium at a pH≥5 of less than or equal to −28 mV.

Said nanoparticle preferably has a zeta potential ζ in aqueous medium at a pH≥6.5, more particularly at a pH≥7 and especially at a pH≥8, of less than or equal to −30 mV.

The luminescent particles of the invention and their synthesis pathway prove advantageous in a number of regards.

This new synthesis pathway relies on the use of bulky tetraalkylammonium counterions.

The inventors thus found that the use of these bulky counterions in the synthesis of nanoparticles based on rare earth ions provides the particles in solution with improved colloidal stability and especially prevents the phenomena of flocculation of the particles.

As set out earlier, the stability of the particles in solution is particularly critical for meeting the requirements in terms of reproducibility for the use of these particles as probes for in vitro or ex vivo diagnosis.

Without wishing to be tied by the theory, this improvement in stabilization, resulting from the use of tetraalkylammonium counterions, as compared, for example, to the use of sodium ions, is linked to the difference in zeta potential of the particles.

The "zeta potential", or ζ, may be defined as the difference in potential that exists between the bulk of the solution and the slipping plane of the particle. It is representative of the stability of a suspension. The slipping plane (or hydrodynamic radius) corresponds to an imaginary sphere around the particle, within which the solvent moves with the particle when the particles move in the solution. The zeta potential may be determined by techniques which are known to a person skilled in the art, for example by moving the particle with its solubilization layer in an electric field, as detailed later on in the text.

As illustrated in the examples which follow, the use of the tetraalkylammonium counterions in fact induces a negative zeta potential of the particle with an increased absolute value by comparison, for example, with the use of sodium counterions. This negative zeta potential of the nanoparticles, of less than or equal to −28 mV, more particularly less than or equal to −30 mV, in aqueous medium at a pH≥5, more particularly at a pH≥6.5, increases the phenomena of mutual electrostatic repulsion of the nanoparticles in aqueous solution, thereby allowing the flocculation phenomena to be suppressed. Indeed, it is known empirically by a person skilled in the art that a zeta potential with a high absolute value, more particularly of more than 28 mV, makes it possible in general to suppress the flocculation effects in media with a low ionic strength.

Therefore, as detailed later on in the text, the nanoparticles of the invention, having tetraalkylammonium cations at the surface, possess a zeta potential, ζ, in aqueous medium at a pH≥5 of less than or equal to −28 mV. More particularly, the nanoparticles of the invention, having tetraalkylammonium cations at the surface, possess a zeta potential in aqueous medium at a pH≥6.5 of less than or equal to −30 mV.

It is understood that the measurements of zeta potential are made after purification of the aqueous suspension of the particles, and thus for an aqueous suspension having an ionic conductivity of strictly less than 100 $\mu S \cdot cm^{-1}$.

The ionic conductivity of the suspension, which allows the level of ions present in said suspension to be assessed, may be measured at an ambient temperature (25° C.) by any known conductimeter.

According to another of its aspects, therefore, the invention provides a colloidal aqueous suspension comprising luminescent particles of the invention.

A suspension of the invention therefore exhibits excellent properties of colloidal stability.

Furthermore, in terms of synthesis, the particles of the invention are synthesized directly in aqueous medium, and the synthesis protocol requires solely a coprecipitation reaction. The preparation of the nanoparticles of the invention is therefore able advantageously to eliminate the steps of removal of organic solvents and of transfer of the nanoparticles into other solvents. In addition, the synthesis of the nanoparticles according to the invention may advantageously be performed at ambient temperature.

In addition, as detailed later on in the text, the orthovanadate ions ($VO_4^{3-}$) used in the coprecipitation reaction to form the nanoparticles of the invention may advantageously be generated in situ from a metavanadate salt, for example ammonium metavanadate ($NH_4VO_3$) or sodium metavanadate ($NaVO_3$), with addition of two equivalents of strong base, advantageously of tetraalkylammonium hydroxides.

The use of metavanadate as a precursor advantageously allows the introduction of the bulky tetraalkylammonium counterions as counterions of the strong base that is used. The technique of synthesizing the particles according to the invention therefore exhibits very high colloidal stability.

Lastly, as detailed below, the particles of the invention can be easily coupled to targeting agents for diagnostic purposes, in vivo, ex vivo or in vitro, via various functionalization/coupling reactions. The nanoparticles synthesized according to the invention therefore find particularly advantageous application as probes which allow the detection and/or quantification, ex vivo or in vitro, in biological samples, with excellent reproducibility.

According to another of its aspects, therefore, the invention provides for the use of particles according to the invention, more particularly coupled to at least one targeting agent, as a diagnostic agent, more particularly as a diagnostic agent in vitro or ex vivo.

According to yet another of its aspects, it relates to a diagnostic kit, more particularly for in vitro or ex vivo diagnosis, in other words a kit for in vitro or ex vivo detection and/or quantification of a substance of biological or chemical interest in a sample, which comprises at least luminescent particles according to the invention, more particularly in the form of a colloidal aqueous suspension.

In the remainder of the text, the term "nanoparticle according to the invention" will refer more simply to the nanoparticle of the aforesaid formula (I) on whose surface there are tetraalkylammonium cations located.

Furthermore, the expression "functionalized nanoparticle" is used to denote the nanoparticle according to the invention that is also surface-functionalized by one or more groups such as, for example, citrate, polyacrylic acid (PAA), aldehyde functions, carboxylic acid functions (COOH), amine functions, etc.

Lastly, the expression "coupled nanoparticle" will be employed to denote the nanoparticle of the invention at the end of its coupling, after surface functionalization, with one or more targeting agents, such as proteins, antibodies, DNA, RNA, aptamer, etc., as detailed later on in the text.

Other characteristics, variants and advantages of the particles according to the invention, of the process for synthesizing them and of using them as probes for diagnosis, will emerge more clearly on a reading of the description, the examples, and the figures which follow, which are given by way of illustration and not in limitation of the invention.

In the remainder of the text, the expressions "between . . . and . . . ", "ranging from . . . to . . . " and "varying from . . . to . . . " are equivalent and mean that the end points are included, unless otherwise specified.

Unless otherwise indicated, the expression "comprising a" should be understood as "comprising at least one".

Luminescent Particles

As specified above, the luminescent particles of the invention comprise, or even are formed of, a nanoparticle of formula $A_{1-x}Ln_xVO_{4(1-y)}(PO_4)_y$ (I) in which A, x, Ln and y are as defined above, bearing on its surface tetraalkylammonium cations.

The immobilization of the tetraalkylammonium cations on the surface of the nanoparticles of the invention results more particularly from electrostatic interactions between the negatively charged surface ions ($O^{2-}$) of the nanoparticle of formula (I) and the positively charged tetraalkylammonium counterions.

Accordingly, the tetraalkylammonium cations are associated directly with the nanoparticle via electrostatic interactions with the negatively charged surface ions of the nanoparticle. More particularly, the immobilization of the tetraalkylammonium cations on the surface of the nanoparticle does not employ any "spacer" group.

By "tetraalkylammonium" cations are meant very particularly tetra($C_1$-$C_6$)alkylammonium cations, in other words cations of formula $NR_4^+$ where R, which are identical or different, represent a $C_1$-$C_6$-alkyl, more particularly $C_1$-$C_4$-alkyl, group.

The "tetraalkylammonium" cations are preferably tetra ($C_1$-$C_3$)alkylammonium cations, in other words cations of formula $NR_4^+$ where R, which are identical or different, represent a $C_1$-$C_3$-alkyl group.

By "$C_1$-$C_6$-alkyl" is meant a saturated, linear or branched aliphatic group comprising 1 to 6 carbon atoms. Examples include the groups methyl, ethyl, propyl, butyl, isopropyl, isobutyl, tert-butyl, etc.

The tetraalkylammonium cations are preferably selected from the cations tetramethylammonium, tetraethylammonium, tetrapropylammonium, tetrabutylammonium, and mixtures thereof.

According to one particular embodiment, the cations present on the surface of the nanoparticles of the invention are tetramethylammonium cations.

As indicated above, the tetraalkylammonium cations are present at the surface of the nanoparticles of the invention in an amount sufficient to obtain the desired result in terms of colloidal stability of the aqueous suspension of said synthesized particles, in other words the desired value of the zeta potential.

The tetraalkylammonium cations present on the surface of the nanoparticles of the invention can be present at from 100 to 10 000 tetraalkylammonium cations per nanoparticle.

The nanoparticles of the invention therefore conform very particularly to the following formula (I'):

$$A_{1-x}Ln_xVO_{4(1-y)}(PO_4)_y \cdot (NR_4^+)_z \qquad (I')$$

in which:
A is selected from Y, Gd, La, and mixtures thereof, A preferably representing Y;
Ln is selected from Eu, Dy, Sm, Nd, Er, Yb, and mixtures thereof, Ln preferably representing Eu;
$0 < x < 1$, more particularly $0.2 \leq x \leq 0.6$, and very particularly x being 0.4;
$0 \leq y < 1$;
R, which are identical or different, are as defined above, representing preferably a $C_1$-$C_3$-alkyl and more particularly methyl group; and z represents the number of tetraalkylammonium cations $NR_4^+$ located on the surface of said nanoparticle, z more particularly being between 100 and 10 000.

According to one particular embodiment, the nanoparticle conforms to the aforementioned formula (I) or (I') in which y is 0.

In other words, the nanoparticle of the invention has the formula $A_{1-x}Ln_xVO_4$ (II), on the surface of which there are tetraalkylammonium cations located.

Accordingly, a nanoparticle of the invention may conform very particularly to the formula $A_{1-x}Ln_xVO_4 \cdot (NR_4^+)_z$ (II'), in which A, x, Ln, R, and z are as defined above.

According to one particular embodiment, A in the aforementioned formula (I), (I'), (II) or (II') represents yttrium (Y).

According to another particular embodiment, Ln in the aforementioned formula (I), (I'), (II) or (II') represents Eu.

Accordingly, in one particular variant embodiment, the particles of the invention are formed wholly or partly of a nanoparticle of formula $Y_{1-x}Eu_xVO_4$ (III), where $0<x<1$, said nanoparticle having tetraalkylammonium cations at the surface.

Very particularly, a nanoparticle of the invention may conform very particularly to the formula $Y_{1-x}Eu_xVO_4 \cdot (NR_4^+)_z$ (III'), in which x, R, and z are as defined above.

According to one particular embodiment, the product of the degree of doping, x, with Ln ions, more particularly with europium (Eu), and the quantum yield of the emission by the nanoparticle is maximized.

More particularly, this is useful when optical excitation of the Ln ions by direct excitation is expected, i.e., in resonance with the electronic states of these ions, and not by excitation of the matrix $AVO_{4(1-y)}(PO_4)_y$, and subsequent transfer of energy to these ions.

This optimization of the product of the degree of doping x with Ln ions and the quantum yield may be performed by using a high level of doping with Ln ions, for example of between 0.2 and 0.6, and especially of 0.4, but without reducing the quantum yield, more particularly by limiting the processes of transfer between doping ions that lead to an extinction of concentration. More particularly, in order to maintain a high quantum yield, it is necessary for the crystallinity of the particle not to be perfect. The reason is that excellent crystallinity promotes the processes of transfer between doping ions, more particularly when these ions are in immediate proximity to one another, as is the case for high levels of doping, and it consequently promotes the processes of de-excitation of the ions by nonradiative processes linked to the solvent. More particularly, a process of synthesis at ambient temperature, or at least at a temperature not exceeding 600° C., is favorable for the imperfect crystallinity that is required for these nanoparticles.

The crystallinity of the nanoparticles is considered to be "imperfect" when the coherence length, determined by the X-ray diffractogram in at least one given crystallographic direction, is less than 80% of the size of the particle in this direction, as measured from transmission electron micrographs. Different types of imperfect crystallinity may be considered: polycrystallinity, defects or porosity.

By way of example, the nanoparticle may be of formula $Y_{0.6}Eu_{0.4}VO_4$ with tetraalkylammonium cations located on the surface. More particularly, it may conform to the formula $Y_{0.6}Eu_{0.4}VO_4 \cdot (NR_4^+)_z$, with z representing the number of tetraalkylammonium cations.

It is understood that the various embodiments referred to above, especially with regard to the nature of the photoluminescent nanoparticle and the surface tetraalkylammonium cations, can be combined.

By way of example, a photoluminescent particle according to the invention may be formed of a nanoparticle of formula $Y_{0.6}Eu_{0.4}VO_4$ with tetramethylammonium cations immobilized on its surface.

The nanoparticles of the invention very particularly have an elongated ellipsoidal overall shape ("prolate", as it is termed).

The size may be measured by transmission electron microscopy. The transmission electron micrographs allow determination of the shape of the nanoparticles (elongated ellipsoids) and deduction of the mean dimensions of the two axes of the ellipsoid. It is generally thought that the third axis of the ellipsoid, which is not visible in the transmission micrographs, which are 2D projections, has a length equal to that of the smallest axis.

The nanoparticles of the invention, with an elongated ellipsoidal shape, may have a length of the major axis, a, of between 20 and 60 nm; and a length of the minor axis, b, of between 10 and 30 nm. More particularly, the nanoparticles of the invention may have a mean major axis length value, a, of 40 nm and a mean minor axis length value, b, of 20 nm.

As set out above, the luminescent particles according to the invention allow access to aqueous suspensions which exhibit very high colloidal stability. It should be noted that this stability is substantial even in media of high ionic strength, as is the case in the synthesis medium even before purification (ionic strength greater than 0.1 M). More particularly, an aqueous suspension of particles according to the invention exhibits little, or no, phenomenon of flocculation.

More particularly, the particles according to the invention with tetraalkylammonium cations present on their surface have a zeta potential, $\zeta$, of less than or equal to −28 mV in an aqueous medium with a pH≥5, more particularly with a pH≥5.5, and having an ionic conductivity of strictly less than 100 μS·cm$^{-1}$.

In other words, the absolute value of the zeta potential, referred to as $|\zeta|$, of the particles of the invention in aqueous medium with a pH≥5, more particularly with a pH≥5.5, is greater than 28 mV.

The "zeta potential" is one of the elements representative of the stability of a suspension. It may, for example, be measured directly, using a Zetasizer Nano ZS instrument from Malvern. This instrument employs optical devices to measure the rates of displacement of the particles as a function of the electrical field applied to them.

The nanoparticles of the invention very particularly possess a zeta potential of less than or equal to −28 mV, preferably less than or equal to −30 mV, in an aqueous medium with a pH≥6, more particularly with a pH≥6.5, and an ionic conductivity of strictly less than 100 μS·cm$^{-1}$.

More particularly, the nanoparticles of the invention possess a zeta potential of less than or equal to −30 mV in an aqueous medium with a pH≥6.5, more particularly with a pH≥7, especially with a pH≥8, and an ionic conductivity of strictly less than 100 μS·cm$^{-1}$.

The nanoparticles according to the invention are primarily crystalline and polycrystalline in nature, more particularly with a mean crystallite size, deduced by X-ray diffraction as detailed in the examples below, of between 3 and 40 nm.

According to one particular embodiment of the invention, the nanoparticles according to the invention are coupled (or grafted) to at least one targeting agent, for the purpose especially of their use as probes in diagnostic techniques, more particularly in in vitro or ex vivo diagnostic techniques, for detecting and/or quantifying biological species in a biological sample.

In other words, the particles of the invention may comprise at least one targeting agent immobilized on the surface of the nanoparticle.

The targeting agents may be of various kinds, as detailed in the rest of the text, depending on the desired application of the luminescent particles of the invention.

Preparation of the Particles

As set out before, the invention, in another of its aspects, further provides a method for preparing luminescent particles comprising a nanoparticle of formula:

$$A_{1-x}Ln_xVO_{4(1-y)}(PO_4)_y \quad (I)$$

in which:
- A is selected from yttrium (Y), gadolinium (Gd), lanthanum (La), and mixtures thereof, with A preferably representing Y;
- Ln is selected from europium (Eu), dysprosium (Dy), samarium (Sm), neodymium (Nd), erbium (Er), ytterbium (Yb), and mixtures thereof, with Ln preferably representing Eu;
- $0<x<1$; and
- $0 \leq y<1$ by coprecipitation reaction, in aqueous medium, from precursors of said elements A and Ln, and in the presence of orthovanadate ions ($VO_4^{3-}$) and optionally phosphate ($PO_4^{3-}$) ions; said reaction being performed in the presence of an effective amount of tetraalkylammonium cations.

More particularly, the invention provides a process for preparing luminescent particles comprising a nanoparticle of formula (I'):

$$A_{1-x}Ln_xVO_{4(1-y)}(PO_4)_y \cdot (NR_4^+)_z \quad (I')$$

in which:
- A represents Y, Gd, La, and mixtures thereof, with A preferably representing Y;
- Ln is selected from Eu, Dy, Sm, Nd, Er, Yb, and mixtures thereof, with Ln preferably representing Eu;
- $0<x<1$;
- $0 \leq y<1$;
- R, which are identical or different, are as defined before, and preferably represent a $C_1$-$C_3$-alkyl group; and
- z represents the number of tetraalkylammonium cations $NR_4^+$ located on the surface of said nanoparticle.

The invention very particularly provides a method for preparing luminescent particles comprising a nanoparticle of formula (II), (II'), (III) or (III') as defined before.

The precursors of the elements A and Ln may take the form, conventionally, of salts of said elements, as for example of nitrates, chlorides, perchlorates or acetates, more particularly nitrates. The precursors of the elements A and Ln, and their amount, are of course selected appropriately with regard to the nature of the nanoparticle desired.

For example, the synthesis of nanoparticles of formula $Y_{1-x}Eu_xVO_4$ (III) may employ yttrium and europium precursor compounds in the form of the nitrates of yttrium ($Y(NO_3)_3$) and of europium ($Eu(NO_3)_3$).

According to one essential feature of the method of the invention, the coprecipitation reaction is carried out in the presence of an effective amount of tetraalkylammonium cations.

The tetraalkylammonium cations are very particularly as defined before. They are preferably selected from tetramethylammonium, tetraethylammonium, tetrapropylammonium and tetrabutylammonium cations and mixtures thereof. The cations in question are preferably tetramethylammonium cations.

By "effective amount" is meant, very particularly, that the cations are employed in an amount sufficient to obtain the desired result in terms of colloidal stability of the aqueous suspension of said synthesized particles.

More particularly, the tetraalkylammonium cations are employed in an amount such that the nanoparticles obtained at the outcome of the method of the invention exhibit a zeta potential as indicated before. As illustrated in example 1 hereinafter, the tetraalkylammonium cations in the coprecipitation reaction according to the invention are counterions to the orthovanadate ($VO_4^{3-}$) and optionally phosphate ($PO_4^{3-}$) ions (where $y \neq 0$).

According to one particularly preferred embodiment, the orthovanadate ions ($VO_4^{3-}$) are generated in situ from a metavanadate salt, preferably ammonium metavanadate ($NH_4VO_3$).

The orthovanadate ions may very particularly be formed in situ by reaction of said metavanadate salt with a base (more specifically with two equivalents of strong base).

More particularly, the base employed for the in situ formation of the orthovanadate ions from the metavanadate salt is a source of tetraalkylammonium cations. It may, for example, be a tetraalkylammonium hydroxide, as for example tetramethylammonium hydroxide.

The use of a metavanadate salt such as ammonium metavanadate, for example, for synthesizing the nanoparticles according to the invention proves particularly advantageous, by comparison with the use of sodium orthovanadate, in that it obviates the reproducibility problems associated with variations in the carbonate content of sodium orthovanadate.

By way of example, the synthesis reaction from ammonium metavanadate and tetramethylammonium hydroxide is represented in example 1.

Consideration may also be given to using alkylammonium metavanadate (not available commercially) and another strong base, such as ammonium hydroxide.

The presence of tetraalkylammonium ions at the surface of the nanoparticles advantageously allows not only a high colloidal stability at the outcome of the synthesis but also stability of the particles formed all along the synthesis and thus much better reproducibility of the synthesis method itself.

The method for preparing the particles according to the invention may more particularly employ at least the following steps, namely:
(i) providing an aqueous solution, called solution (1), comprising orthovanadate ions ($VO_4^{3-}$), and optionally phosphate ions ($PO_4^{3-}$), and tetraalkylammonium cations;
(ii) admixing the aqueous solution (1) with an aqueous solution, called solution (2), comprising said precursors of the elements A and Ln, more particularly in the form of salts, especially nitrates, under conditions conducive to the formation by coprecipitation of the nanoparticles of formula (I); and
(iii) recovering said nanoparticles of formula (I) with tetraalkylammonium cations located on their surface that are formed at the end of step (ii).

The aqueous solution (1) may very particularly be prepared by mixing at least one metavanadate salt, more particularly ammonium metavanate, and at least one base which is a source of tetraalkylammonium cations, as for example a tetraalkylammonium hydroxide.

In the case of phosphate ions, a phosphate salt is added, such as sodium phosphate or ammonium phosphate.

Thus, according to one particularly advantageous variant embodiment, the method of the invention comprises at least the steps of:

(i) preparing an aqueous solution (1) by mixing, in an aqueous medium, a metavanadate salt, more particularly ammonium metavanadate ($NH_4VO_3$), and optionally a phosphate salt, and a base which is a source of tetraalkylammonium cations, more particularly a tetraalkylammonium hydroxide;

(ii) admixing the aqueous solution (1) with an aqueous solution (2) comprising said precursors of the elements A and Ln, more particularly in the form of salts, especially nitrates, under conditions conducive to the formation by coprecipitation of the nanoparticles of formula (I); and (iii) recovering the nanoparticles of formula (I) with tetraalkylammonium cations located on their surface that are formed at the end of step (ii).

According to one particular embodiment, the addition of solution (2) to solution (1) in step (ii) is performed dropwise.

According to another variant embodiment, the solution (2) may be added to the solution (1) in one go, and not dropwise.

The aqueous medium of the solutions (1) and (2) is very particularly formed by water.

In one particular embodiment, the aqueous solution (2) containing the precursors of the elements A and Ln may further comprise complexing agents for these elements, such as citrate, as for example tetraalkylammonium citrate.

It is within the capabilities of a person skilled in the art to appropriately adjust the amounts of the various reactants, more particularly the precursors of the orthovanadate and optionally phosphate ions and of said elements A and Ln, with regard to the desired nature of the nanoparticle of formula (I) according to the invention.

More particularly, it is necessary to respect the stoichiometric proportions of the various reactants according to the formulae (I), (I'), (II), (II'), (III) and (III'). When optical excitation of the Ln ions is envisaged by direct excitation, i.e., in resonance with the electronic states of these ions, and not by excitation of the matrix $AVO_{4(1-y)}(PO_4)_y$, and subsequent transfer of energy to these ions, as set out before, it is preferable for the value of x to be high, preferably between 0.2 and 0.6, and preferably 0.4.

Advantageously, the method for preparing the particles of the invention does not require any heating of the solution, in contrast, in particular, to the hydrothermal techniques proposed in publications [13]-[18]. More particularly, all of steps (i) to (iii) for synthesizing the particles according to the invention may be advantageously carried out at ambient temperature (20-25° C.).

Nevertheless, methods for preparation at a higher temperature, of hydrothermal type, for example, may produce nanoparticles with similar crystallinity, provided that the temperature does not exceed 600° C., thus permitting access to nanoparticles exhibiting an imperfect crystallinity as set out before and thus the realization of a high quantum yield.

Step (iii) very particularly involves purifying the solution of particles obtained, especially in order to remove the excess of counterions.

The purification steps may very particularly include steps of dialysis or centrifugation and redispersion of the particles in an aqueous medium, by sonication, for example.

The particles may be redispersed in an aqueous medium, more particularly in water. As set out before, the aqueous colloidal suspension of the particles of the invention exhibits very high stability, even after several months of storage.

In another of its aspects, the invention further provides the particles obtained at the outcome of the method as described before.

According to one particular variant embodiment, the invention provides a method for preparing particles formed wholly or partly of a nanoparticle of formula $Y_{1-x}Eu_xVO_4$ (III), with $0<x<1$, comprising at least the steps of:

(i) providing an aqueous solution (1), comprising orthovanadate ions and tetraalkylammonium cations, said aqueous solution (1) being preferably obtained from a mixture, in an aqueous medium, of ammonium metavanadate ($NH_4VO_3$) and a tetraalkylammonium hydroxide;

(ii) admixing the aqueous solution (1) with an aqueous solution, called solution (2), comprising precursors of Y and Eu, more particularly yttrium and europium nitrates, under conditions conducive to the formation by coprecipitation of the nanoparticles of formula (III); and (iii) recovering said nanoparticles of formula (III) with tetraalkylammonium cations located on their surface, as formed at the outcome of step (ii).

According to one particular embodiment, the method may further comprise one or more steps of coupling (grafting) of the particles obtained with one or more targeting agents, with the aim in particular of using them for an in vitro, ex vivo, or in vivo diagnosis technique.

It is within the capabilities of a person skilled in the art to employ coupling/grafting techniques suitable for appropriately preparing the particles with the aim of using them as a diagnostic probe. The amount of targeting agent(s) employed is adjusted with regard to the amount of particles.

The targeting agent may be grafted to the nanoparticle directly or via a spacer (also denoted by the term "linker").

The techniques for coupling (also called grafting) the particles to biomolecules are well known to the person skilled in the art. They generally involve coupling by covalent bonding, by surface complexation, by electrostatic interactions, by encapsulation, or by adsorption. In certain cases, including that of coupling by covalent bonding, the particles may be functionalized beforehand with one or more chemical groups capable, subsequently, of reaction with another chemical group carried by the targeting agent, to form a covalent bond.

Examples of chemical groups which may be present on the surface of the nanoparticles include carboxyl, amino, thiol, aldehyde, and epoxy groups.

For example, the nanoparticles of the invention may be surface-functionalized with citrate, as illustrated in example 4 hereinafter.

According to another particular embodiment, the nanoparticles of the invention may be surface-functionalized with polyacrylic acid (PAA). In the case of functionalization with PAA, the number of coordinate bonds (dative bonds) formed by each molecule of PAA increases in proportion with the length of the PAA. The PAA may, for example, have a degree of polymerization ranging from 3 to 10 000.

The functionalization of the nanoparticles with PAA leads, advantageously, to functionalized nanoparticles, and to nanoparticles resulting from the coupling of these functionalized nanoparticles with one or more targeting agents, that exhibit excellent properties in terms of stability over time.

Amino groups may be provided by molecules such as aminoorganosilanes, for instance aminotriethoxysilane (APTES). The advantage of APTES lies in the fact that, via covalent bonds, it forms a capsule around the nanoparticle. The amines provided by APTES are therefore very stable over time. The amino groups may be converted into carboxyl groups by reaction with succinic anhydride.

Carboxyl groups may be provided by molecules such as citric acid or a polyacrylic acid (PAA).

The carboxyl groups may be activated by any technique known to a person skilled in the art, more particularly by reaction with 1-ethyl-3-(3-dimethylaminopropyl)carbodiimide (EDC) and N-hydroxysuccinimide (NHS), for subsequent reaction with the amine functions on the surface of a polypeptide and formation of a covalent amide bond, when the targeting agent is a protein or an antibody.

The functionalization of the nanoparticles with APTES may take place advantageously after the covering of the nanoparticles with a layer of silica.

Applications

As specified before, the particles synthesized according to the invention, more particularly coupled to at least one targeting agent, find particularly advantageous application as probes or biomarkers in biological samples.

The present invention, in another of its aspects, provides for the use of the particles described before or obtained by the method described before, more particularly coupled to at least one targeting agent, or of a colloidal aqueous suspension of these particles, as a diagnostic agent—that is, for detecting and/or quantifying a substance of biological or chemical interest.

The nanoparticles may especially be used as an in vitro or ex vivo diagnostic agent, in other words for detecting and/or quantifying a substance of biological or chemical interest within a sample, more particularly a biological sample.

The particles of the invention may be coupled with various targeting agents.

By "targeting agent" is meant a compound which allows a bond with a substance which is of biological or chemical interest and whose identification is desired.

The probes according to the invention are very well suited to a wide diversity of biological targets, the specificities being dependent on the nature of the targeting agent or agents grafted to the surface of the nanoparticle.

The targeting agent may more particularly be a polyclonal or monoclonal antibody, an antibody fragment, an oligonucleotide, a peptide, a hormone, a ligand, a cytokine, a peptidomimetic, a protein, a carbohydrate, a chemically modified protein, a chemically modified nucleic acid, a chemically modified carbohydrate targeting a known cell surface protein, an aptamer, an assembly of proteins and DNA/RNA, or a chloroalkane used by HaloTag labels.

According to one particular embodiment, the agent is an antibody or antibody fragment.

Appropriate antibody fragments include at least one variable domain of an immunoglobulin, such as simple variable domains Fv, scFv, Fab, (Fab')$^2$ and other proteolytic fragments or "nanobodies" (single-domain antibodies such as the $V_HH$ fragments obtained from camelid antibodies, or $V_{NAR}$ fragments obtained from fish cartilage antibodies).

The term "antibody" according to the invention includes chimeric antibodies, human or humanized antibodies, recombinant and modified antibodies, conjugated antibodies, and fragments thereof.

According to one particular embodiment, the antibodies or antibody fragments used according to the invention target specific markers of cancerous cells.

The targeting agent may also be derived from a molecule known to bind a cell surface receptor. For example, the targeting fragment may derive from low-density lipoproteins, transferrin, EGF, insulin, PDGF, fibrinolytic enzymes, anti-HER2, anti-HER3, anti-HER4, annexins, interleukins, interferons, erythropoietins or colony-stimulating factors.

The particles coupled to a targeting agent according to the invention may be used in in vitro, ex vivo or in vivo diagnosis techniques involving recognition of a ligand/antiligand pair, examples being biotin or biotinylated compounds/avidin or streptavidin, hapten/antibody, antigen/antibody, peptide/antibody, sugar/lectin, polynucleotide/polynucleotide complement, etc., subject to the proviso that one of the elements in these pairs constitutes the molecule of biological interest, or may also be coupled to the molecule of biological interest.

An example of coupling of particles according to the invention of type $Y_{0.6}Eu_{0.4}VO_4$ to a protein, streptavidin, and to an antibody is given in example 4 hereinafter.

The particles according to the invention allow the determination, in a biological sample, for example, of the presence of the molecule of interest, which will enter into association with the targeting agent; the association is revealed by virtue of the luminescence properties of the particles of the invention, after the removal, in particular, of targeting agents which will not be linked to the molecule of interest.

The particles of the invention may thus be employed for detecting and/or quantifying concentrations of biomarkers, antibodies, DNA, RNA, etc., in biological samples.

The biological samples may for example be selected from the list including blood, serum, plasma, saliva, urine, cerebrospinal fluid, etc.

The in vitro or ex vivo diagnostic techniques able to employ the particles of the invention are widely known to a person skilled in the art. As examples, they may include the following techniques: immunoassay, immunolabeling, immunohistochemistry, immunocytochemistry, immunomarking, Western blot technique, "dot blot" technique, flow cytometry, the FACS method of fluorescence-activated cell sorting, and more generally any type of detection of biomolecules on the surface of cells which are living or fixed or on cryogenic or noncryogenic tissue sections, ELISA, ELOSA, ELISPOT, multiplex/multidetection analysis, fluorescence in situ hybridization or FISH, etc.

The particles of the invention may further be employed in a method for detecting DNA by hybridization or for detecting RNA by RT-PCR followed by hybridization.

The carriers for in vitro or ex vivo analysis may be of various kinds. They may be plates, multiwell plates, microplaques, gels, membranes, strips, microchannels, etc.

Detection may be performed by any customary device, generally comprising a radiation source for excitation of the particles, as for example a laser illumination device, more particularly a monochromatic device, and a means for detecting the luminous intensity emitted by the particles, in the form, for example, of a camera such as a CCD camera, an electron multiplication CCD (EM-CCD) camera or a single photodetector, especially of the photomultiplier or photodiode type.

The diseases which can be diagnosed with the particles of the invention are not limited, and include any diseases revealed by the presence of one or more markers specific for the disease, comprising a molecule of biological interest for which there is a specific bonding partner.

Examples include infectious (bacterial, parasitic or viral) diseases (such as AIDS), inflammatory and autoimmune diseases, cardiological, neurological or oncological diseases (for example, solid cancers such as breast cancer or prostate cancer).

In another of its aspects, the invention further provides a kit for in vitro, ex vivo or in vivo diagnosis, comprising at least particles according to the invention or an aqueous colloidal suspension of these particles.

The invention more particularly provides a kit for in vitro or ex vivo detection and/or quantification of a substance of biological or chemical interest in a sample, comprising at least particles according to the invention or a colloidal aqueous suspension of these particles.

The detection kit may very particularly comprise:
- a carrier with a targeting agent for the analyte for detection/quantification immobilized on its surface, for example a first antibody, called "capture antibody", specific to the substance of biological or chemical interest to be detected/quantified; and
- one or more containers comprising at least nanoparticles according to the invention and at least a targeting agent in a form coupled or not coupled to the nanoparticles.

The carrier may be of any type, especially of glass or of plastic, such as a plate, a column, a gel, magnetic beads, etc., as set out before. It is advantageously a multiwell plate. The immobilization is typically realized by adsorption or by covalent bonding on the surface of the wells.

According to a first alternative, the kit may comprise nanoparticles according to the invention which are already coupled to a targeting agent, more particularly to antibodies, referred to as "visualizing antibodies", to distinguish them from the capture antibodies immobilized on the carrier.

Figure 6:
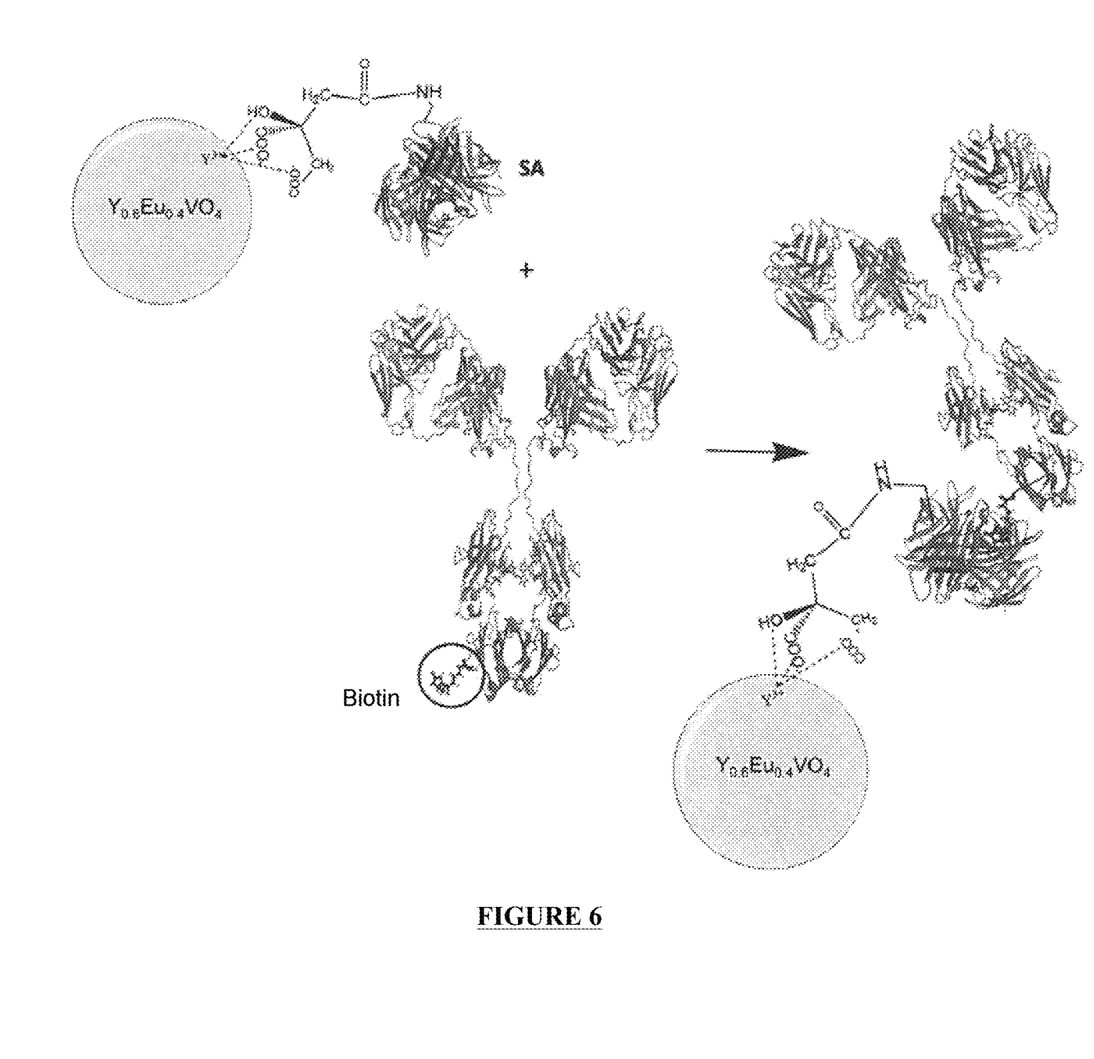
FIG. 6: Schematic representation of the coupling of the nanoparticles coupled with streptavidin with a biotinylated antibody.

The antibody-coupled nanoparticles employed in a kit according to the invention may be obtained for example—as described in example 4 and illustrated in FIG. 6—by coupling of the nanoparticles coupled with streptavidin, with biotinylated antibodies, or else directly by coupling of the antibodies on the nanoparticles functionalized with citrate or with polyacrylic acid.

Alternatively, the kit may comprise a plurality of containers comprising, in isolation, the nanoparticles according to the invention and the targeting agent, and from which the practitioner is able to prepare nanoparticles according to the invention coupled to the targeting agent.

For example, the kit may comprise a first container comprising the nanoparticles of the invention functionalized with citrate or polyacrylic acid, and a second container comprising the biotinylated antibodies; preparation of the nanoparticles coupled to the antibodies involves activating the carboxyl functions contained in the first container, as described in example 4, followed by mixing the contents of the first and second containers.

Of course, a detection kit according to the invention comprising particles according to the invention is not limited to the kit variants described above.

The particles of the invention may further be employed, according to another embodiment, as a diagnostic agent intended for in vivo optical imaging or else as an agent which amplifies treatments in vivo by irradiation.

According to yet another of its aspects, the present patent application thus provides luminescent particles according to the invention, coupled or not coupled to at least one targeting agent, for use in vivo as a diagnostic agent intended for optical imaging or for magnetic resonance imaging, when the particles include gadolinium, or for X-ray imaging. More particularly they may be used as an MRI contrast agent.

The nanoparticles of the invention may also be used in radiotherapy, owing to their sensitizing power.

According to yet another of its aspects, the present patent application thus provides luminescent particles according to the invention, coupled or not coupled to at least one targeting agent, for use in vivo as an agent for in vivo amplification in the treatment of cancers by means of ionizing irradiation (electrons, protons, X or γ photons, etc.).

The nanoparticles are used accordingly to boost the destructive power of the radiotherapy in the tumor cells, while reducing the toxicity for healthy tissues.

The examples and figures presented below are given solely by way of illustration, and not limitation, of the invention.

FIGURES

It will be appreciated that FIGS. 4 to 6 are diagrams of principle, especially as regards the structure of the surface molecules, which may have a number of configurations other than that shown in these figures.

EXAMPLES

Example 1

Synthesis of $Y_{0.6}Eu_{0.4}VO_4$ Nanoparticles According to the Invention

The source of metavanadate $VO_3^-$ ions used is ammonium metavanadate $NH_4VO_3$, the orthovanadate $VO_4^{3-}$ being obtained in situ following reaction with a base, presently tetramethylammonium hydroxide, $N(CH_3)_4OH$. Yttrium and europium nitrates were used as sources of $Y^{3+}$ and $Eu^{3+}$ ions.

An aqueous solution of 10 mL of 0.1 M $NH_4VO_3$ and 0.2 M $N(CH_3)_4OH$ (solution 1) is freshly prepared.

A volume of 10 mL of another solution of $Y(NO_3)_3$ and of $Eu(NO_3)_3$ with an ion ($Y^{3+}+Eu^{3+}$) concentration of 0.1 M is added dropwise to solution 1 using a syringe driver at a rate of 1 mL/min.

The molar concentration ratio between $Y(NO_3)_3$ and $Eu(NO_3)_3$ is selected according to the desired ratio between ions $Y^{3+}$ and $Eu^{3-}$ in the nanoparticle; typically, the molar ratio $Y^{3+}:Eu^{3+}$ is 0.6:0.4.

When the $Y(NO_3)_2/Eu(NO_3)_3$ solution is added, the solution becomes diffuse and appears white/milky without form- ing precipitate. The synthesis continues until all of the Y(NO$_3$)$_2$/Eu(NO$_3$)$_3$ solution has been added.

The eventual 20 mL solution must now be purified to remove the excess of counterions. To do this, centrifugations (typically three) at 11 000 g (Sigma 3K10, Bioblock Scientific) for 80 minutes, followed in each case by redispersion by sonication (Branson Sonifier 450 operating at 50% with a power of 400 W) are used until the resulting conductivity is strictly less than 100 µS·cm$^{-1}$.

The conductivity is measured using a chemical conductimeter.

The synthesis of Y$_{0.6}$Eu$_{0.4}$VO$_4$ nanoparticles with tetramethylammonium cations immobilized on their surface may be represented schematically as follows:

Two trial syntheses ("synthesis 1" and "synthesis 2") are performed.

Result

Visual observation of the solution of nanoparticles according to the invention, after having been left at rest for 16 hours in a flask, shows a uniformly diffuse solution.

The eventual solution remains very stable in water, even after several months in the final pH of the synthesis (approximately pH 7-9). The solution remains stable, including in the synthesis medium (before the removal of the excess of counterions), but with a high ionic strength (>0.1 M).

The zeta potential of the nanoparticles is determined using a DLS-Zeta Potential instrument (Zetasizer Nano ZS90, Malvern). The results of the zeta potentials measured for the nanoparticles from the two syntheses are collated in table 1 below.

For the observations by transmission electron microscopy (TEM), dilute solutions of nanoparticles are placed on a carbon grid. The observations are made using a Philips CM30 microscope operating at 300 kV with a resolution of 0.235 nm.

Figures 1, 1A, 1B:
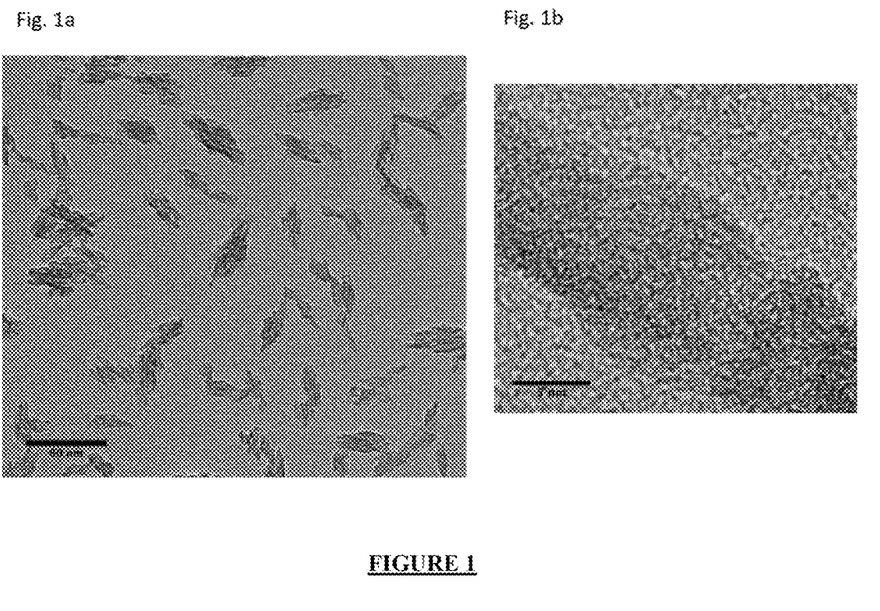
FIG. 1: Micrographs obtained by transmission electron microscopy (TEM) of the nanoparticles obtained according to example 1 (Scale bar: 60 nm (FIG. 1a) and 5 nm (FIG. 1b), respectively)
Figure 2:
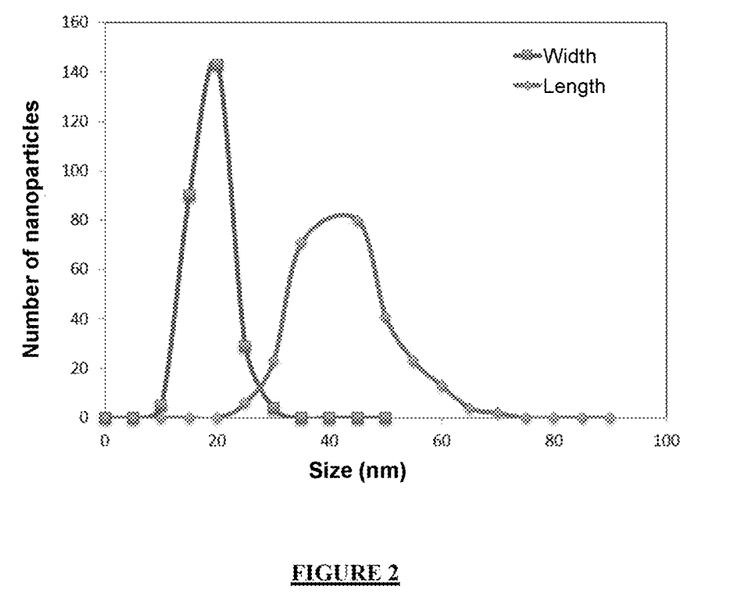
FIG. 2: Size histogram of the nanoparticles, determined from TEM micrographs for a collective of approximately 300 nanoparticles according to example 1.

The observation of the nanoparticles by TEM (FIG. 1) shows the nanoparticles to have an elongated ellipsoidal shape. The dimensions of the nanoparticles are determined from TEM micrographs for a collective of approximately 300 nanoparticles (FIG. 2). The nanoparticles of the invention have a major axis length, a, of between 20 and 60 nm, with an average value of approximately 40 nm, and a minor axis length, b, of between 10 and 30 nm, with an average value of approximately 20 nm.

The TEM micrographs (FIG. 1) do not allow the crystalline planes to be made out, a fact probably attributable to the nanoparticle being composed of a number of crystallites whose size is smaller than the size of the nanoparticle. The primarily crystalline and polycrystalline nature of the nanoparticles is confirmed by X-ray diffraction experiments.

Figure 3:
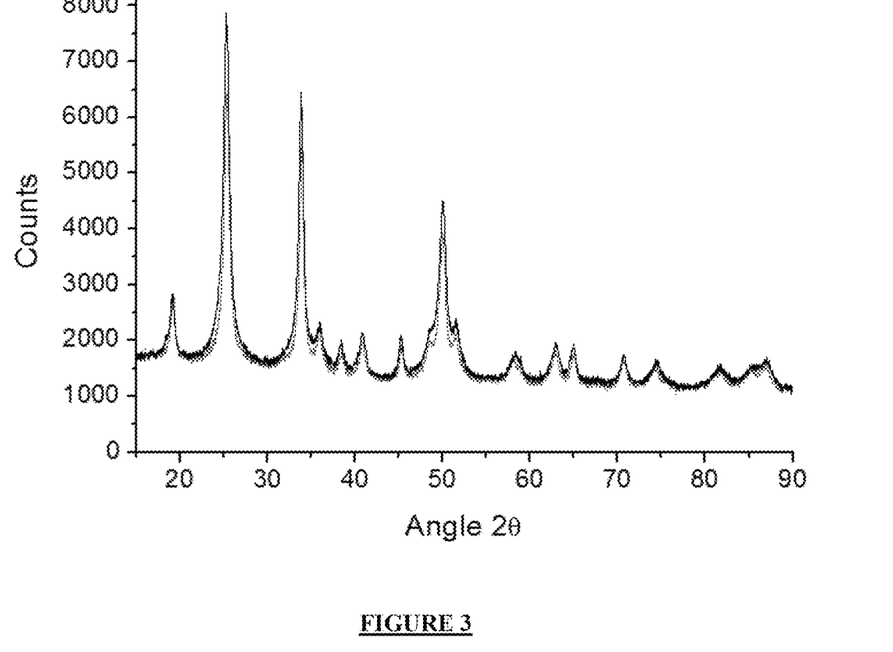
FIG. 3: X-ray diffractograms obtained for the nanoparticles synthesized according to example 1 (black line), and 3 (gray line)

The X-ray diffractogram obtained by means of a Philips X-pert diffractometer using the K$_{\alpha1}$ ray of copper ($\lambda$=1.5418 Å) is represented in FIG. 3. The diffraction intensity is recorded using an X'Celerator area detector (PANalytical).

The coherence length in one crystallographic direction, and therefore the average size of the crystallites making up the nanoparticle in this crystallographic direction, can be estimated from the width of the peaks in the XR diffractogram, by application of the formula of Scherrer. The coherence length values obtained for the various crystallographic directions are between 3 and 40 nm. The coherence length in at least one crystallographic direction is smaller than the size of the nanoparticle in that direction, and from this it may be deduced that the crystallinity of the nanoparticles is imperfect (polycrystallinity, defects or porosity). In the direction (200) (FIG. 3, peak at) 2θ≅25°), the coherence length is 10.2 nm, which is slightly weaker than the coherence length for the nanoparticles of example 3 (11.1 nm).

Example 2 (Not Inventive)

Synthesis of Y$_{0.6}$Eu$_{0.4}$VO$_4$ Nanoparticles from Sodium Metavanadate, without Bulky Counterions For the synthesis by coprecipitation of metal salts, yttrium and europium nitrates were used as sources of Y$^{3+}$ and Eu$^{3+}$ ions. The source of metavanadate VO$_3^-$ ions used is sodium metavanadate NaVO$_3$, the orthovanadate VO$_4^{3-}$ being obtained in situ following reaction with a base, presently sodium hydroxide, NaOH.

An aqueous solution of 10 mL of 0.1 M NaVO$_3$ and 0.2 M NaOH (solution 1) is freshly prepared.

A volume of 10 mL of another solution of Y(NO$_3$)$_3$ and of Eu(NO$_3$)$_3$ with an ion (Y$^{3+}$+Eu$^{3+}$) concentration of 0.1 M is added dropwise to solution 1 using a syringe driver at a rate of 1 mL/min.

The molar concentration ratio between Y(NO$_3$)$_3$ and Eu(NO$_3$)$_3$ is selected according to the desired ratio between ions Y$^{3+}$ and Eu$^{3-}$ in the nanoparticle; typically, the molar ratio Y$^{3+}$:Eu$^{3+}$ is 0.6:0.4.

When the Y(NO$_3$)$_2$/Eu(NO$_3$)$_3$ solution is added, a milky precipitate appears. The synthesis continues until all of the Y(NO$_3$)$_2$/Eu(NO$_3$)$_3$ solution has been added.

The eventual 20 mL solution must now be purified to remove the excess of counterions. To do this, centrifugations (typically three) at 11 000 g (Sigma 3K10, Bioblock Scientific) for 80 minutes, followed in each case by redispersion by sonication (Branson Sonifier 450 operating at 50% with a power of 400 W) are used until the resulting conductivity is strictly less than 100 µS·cm$^{-1}$.

Result

A comparison of the resulting solution with the solution of nanoparticles according to the invention as obtained in example 1 (for the same final concentration of vanadate ions), after 16 hours at rest, shows that, in contrast to the solution from example 1, the solution is less diffuse (less white); a slight deposit has formed on the base of the flask.

The zeta potential of the nanoparticles, determined as described in example 1, is presented in table 1 below.

Example 3 (Not Inventive)

Synthesis of Y$_{0.6}$Eu$_{0.4}$VO$_4$ Nanoparticles from Sodium Orthovanadate, without Bulky Counterions For the synthesis by coprecipitation of metal salts, yttrium and europium nitrates were used as sources of Y$^{3+}$ and Eu$^{3+}$ ions. As a source of orthovanadate ions, VO$_4^{3-}$, sodium orthovanadate Na$_3$VO$_4$ is used.

An aqueous solution of 10 mL of 0.1 M Na$_3$VO$_4$ (solution 1) is freshly prepared. The pH is measured and adjusted if necessary to give a value of between 12.6 and 13.

A volume of 10 mL of another solution of Y(NO$_3$)$_3$ and of Eu(NO$_3$)$_3$ with an ion (Y$^{3+}$+Eu$^{3+}$) concentration of 0.1 M is added dropwise to solution 1 using a syringe driver at a rate of 1 mL/min.

The molar concentration ratio between Y(NO$_3$)$_3$ and Eu(NO$_3$)$_3$ is selected according to the desired ratio between ions Y$^{3+}$ and Eu$^{3-}$ in the nanoparticle; typically, the molar ratio Y$^{3+}$:Eu$^{3+}$ is 0.6:0.4.

When the Y(NO$_3$)$_2$/Eu(NO$_3$)$_3$ solution is added, a milky precipitate appears. The synthesis continues until all of the Y(NO$_3$)$_2$/Eu(NO$_3$)$_3$ solution has been added.

The eventual 20 mL solution must now be purified to remove the excess of counterions. To do this, centrifugations (typically three) at 11 000 g (Sigma 3K10, Bioblock Scientific) for 80 minutes, followed in each case by redispersion by sonication (Branson Sonifier 450 operating at 50% with a power of 400 W) are used until the resulting conductivity is strictly less than 100 µS·cm$^{-1}$.

Results

A comparison of the resulting solution with the solution of nanoparticles according to the invention as obtained in example 1 (for the same final concentration of vanadate ions), after 16 hours at rest, shows that, in contrast to the solution from example 1, the majority of the nanoparticles have deposited on the base of the flask; the upper part of the solution is almost transparent, indicating an absence of diffusion and hence of nanoparticles in solution.

The zeta potential of the nanoparticles, determined as described in example 1, is presented in table 1 below.

The X-ray diffractogram obtained using a Philips X-pert diffractometer is represented in FIG. 3.

As for example 1, the average size of the crystallites making up the nanoparticle in the crystallographic direction (200) may be estimated by application of the formula of Scherrer, and gives a value of between 3 and 40 nm. The size of the crystallites is smaller overall than the dimensions of the nanoparticle, and it can be deduced from this that the nanoparticles synthesized according to example 3 are also polycrystalline.

TABLE 1 comparison of the zeta potential ζ of nanoparticles obtained according to example 1 in accordance with the invention (synthesis based on ammonium metavanadate with bulky counterions), and according to examples 2 and 3 not in accordance with the invention (synthesis based on sodium metavanadate without bulky counterions, and synthesis based on orthovanadate without bulky counterions).

| Examples | Example 1 (inventive) | | Example 2 (not inventive) | Example 3 (not inventive) |
|---|---|---|---|---|
| | Synthesis 1 | Synthesis 2 | | |
| Conductivity (µS/cm) | 93 | 80 | 53 | 66 |
| pH | 4.8 | 5.0 | 5.4 | 9.6 |
| Zeta potential ζ* | −33.3 | −34.6 | −2.30 | −18.00 |

* zeta potential measurements made after purification to give a conductivity <100 µS·cm$^{-1}$ and after dilution in acidic Milli-Q ® water.

The comparison of the zeta potentials of the nanoparticles obtained according to examples 1 to 3 confirm that the nanoparticles according to the invention (example 1) exhibit an improved colloidal stability with |ζ|>30 mV by comparison with the nanoparticles obtained without tetraalkylammonium cations (examples 2 and 3).

An alternative synthesis of the nanoparticles Y$_{0.6}$Eu$_{0.4}$VO$_4$ according to the invention was carried out according to the same protocol as in the synthesis of example 1, with the only difference being that the solution of 10 mL of Y(NO$_3$)$_3$ and Eu(NO$_3$)$_3$ with an ion (Y$^{3-}$+Eu$^{3+}$) concentration of 0.1 M was added to solution 1 not dropwise, but in a single go.

At the end of the synthesis, after purification, the zeta potential is −35 mV at a pH of 7.8.

Example 4

Coupling of the Nanoparticles with the Protein Streptavidin i. Grafting of Citrate to the Surface of the Nanoparticles At the outcome of the synthesis of the nanoparticles according to example 1, the nanoparticle solution is centrifuged at 17 000 g for 3 minutes, to precipitate any nanoparticle aggregates, and the supernatant is recovered.

Approximately 250 µL of Y$_{0.6}$Eu$_{0.4}$VO$_4$ particles with a vanadate ion concentration of 5 mM are removed and are dispersed in 1 mL of a distilled water solution containing the citrate ion (concentration 0.2 M).

The solution is then sonicated for 5 minutes and subsequently centrifuged at 17 000 g for 3 minutes. This step is repeated 3 times.

At the end of this grafting, the particles are dispersed in the distilled water, a solvent in which they are stable.

The functionalization of the nanoparticles with citrate may be replaced by functionalization with PAA (for example, with a degree of polymerization of between 3 and 10 000) by employing a salt of PAA, as for example a sodium or ammonium salt.

Figures 4, 4A, 4B:
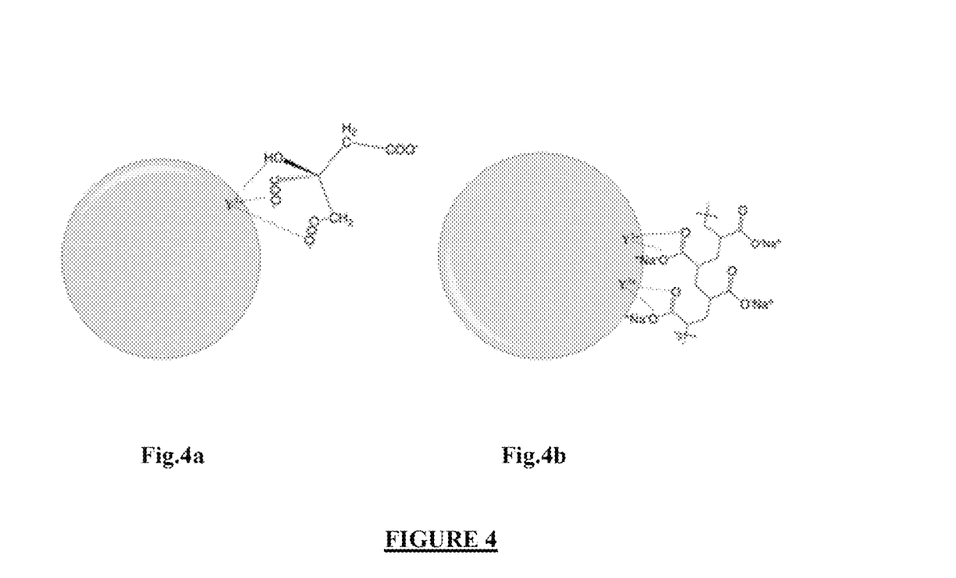
FIG. 4: Schematic representation of the nanoparticles of the invention functionalized with citrate (FIG. 4a) or with polyacrylic acid (PAA) (FIG. 4b). For clarity, a single citrate or PAA molecule is represented. It will be appreciated that each nanoparticle may contain numerous PAA or citrate molecules on its surface.

FIG. 4 shows schematically the nanoparticles of the invention functionalized with (a) citrate and (b) polyacrylic acid.

ii. Coupling of the Nanoparticles with Streptavidin

The nanoparticles (NPs) grafted with the citrate ions are centrifuged at 16 000 g for 1 hour, and the pellet is then recovered.

The coupling of the nanoparticles, grafted on their surface with citrate, with streptavidin is carried out according to the following protocol:

1. Freshly prepare a mixed solution of EDC[1]/Sulfo-NHS[2] (concentrations 30 and 30 mg/mL, respectively) in MES buffer[3] (pH 5-6).
2. By sonication (ultrasound bath) disperse the pellet of the NPs in 250 µL of the solution prepared in step 1. Since the losses during the centrifugations are low, the concentration of vanadate ions remains around 5 mM, giving a nanoparticle concentration of 48 nm.
   (The vanadate concentration of the nanoparticle solutions was determined by dissolving the particles in an acidic medium, followed by colorimetric determination of the concentration of vanadate ions, as described in the reference Abdesselem et al., ACS Nano 8, 11126-11137 (2014). The molar concentration of the nanoparticles was determined from the concentration of vanadate ions as described in the reference Casanova et al., Appl. Phys. Lett 89, 253103 (2006).)
3. Prepare a solution of streptavidin (SA) at 100 nm in phosphate buffer pH 7.4 with NaCl at 10 mM. Dilute the streptavidin solution to a concentration determined by the desired number of proteins grafted per nanoparticle (for a streptavidin:NPs ratio of 1:1, 5:1 and 10:1, select, respectively, concentrations of 4.8 nm, 24 nm and 48 nm). Add 250 µL of this solution to the nanoparticle solution.
4. Incubate for between 2 and 4 h at ambient temperature.
5. Add 1 mL of PBST[4] and vortex.
6. Carry out centrifugation at 6 500 g for 30 min and recover the pellet to remove the proteins not coupled to the NPs. Discard all of the supernatant. Redisperse the NPs coupled to the proteins in 1 mL of PBST and sonicate in an ultrasound bath. Repeat this step twice.

7. Recover the NPs coupled to the proteins in 250 μL of PBS[5] with 1% of BSA[6].
8. Keep at 4° C. for immediate use or aliquot and keep at −80° C.

Figure 5:
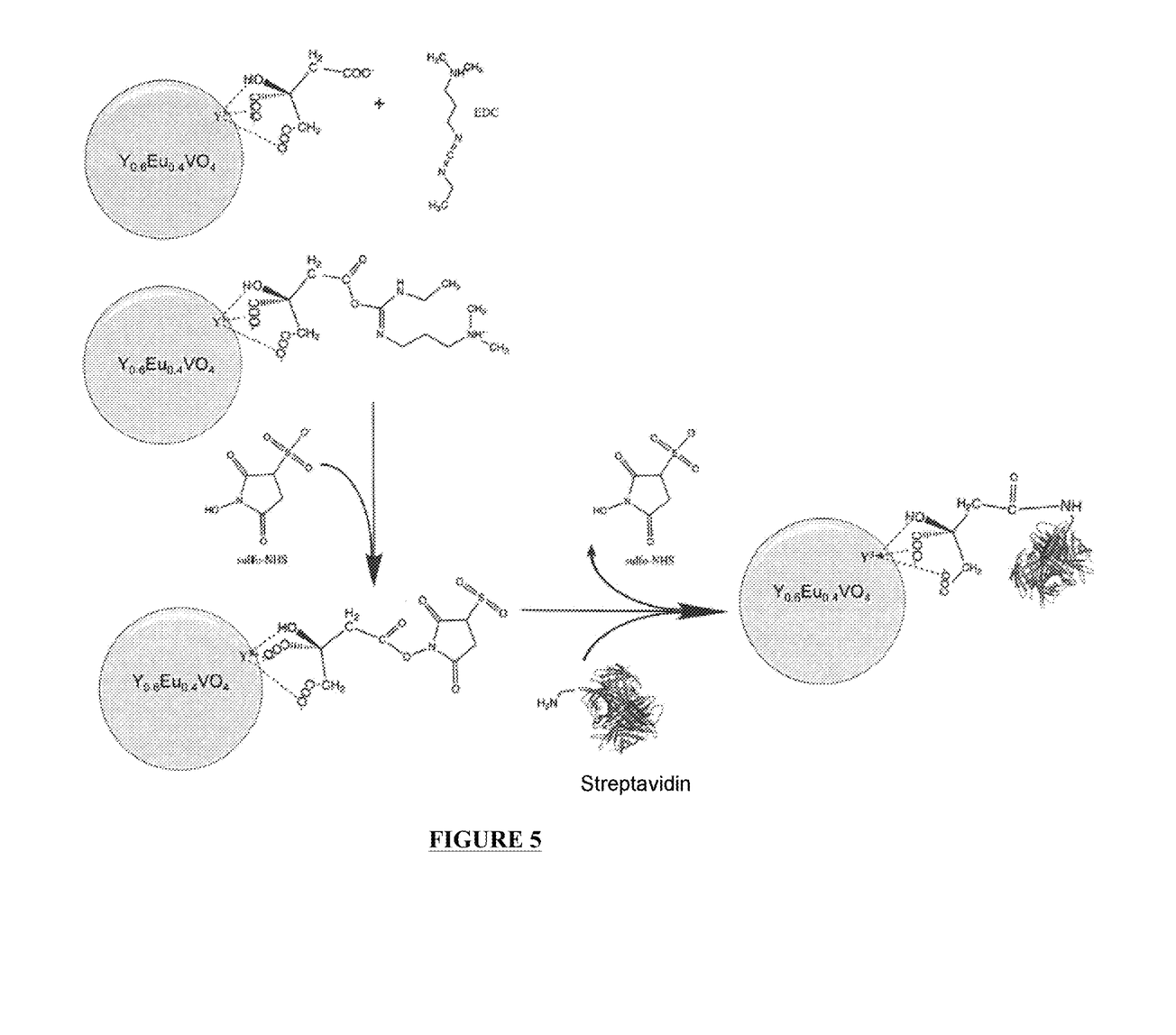
FIG. 5: Schematic representation of the reactions for coupling a nanoparticle according to the invention with streptavidin, according to example 4.

The coupling of the nanoparticles with streptavidin is represented schematically in FIG. 5.

Materials used for the functionalization trial:
[1] N-(3-Dimethylaminopropyl)-N'-ethylcarbodiimide hydrochloride (EDC) (Sigma, cat #E1769).
[2] N-Hydroxysulfosuccinimide sodium salt (Sulfo-NHS) (Sigma, cat #56485).
[3] 2-(N-Morpholino)ethanesulfonic acid (MES) (10 mM, pH 5-6).
[4] Phosphate-buffered saline pH 7.4 (10 mM NaCl)+0.05% Tween 20 (PBST).
[5] Bovine serum albumin (BSA) (Sigma, cat #A3059).
[6] Phosphate-buffered saline (PBS) (pH 7.4, 10 mM NaCl).

The number of molecules of streptavidin (SA) per nanoparticle (NP), denoted R, characterized at the end of the coupling protocol, is determined by assaying the streptavidin by the BCA method, according to the protocol detailed above.

Protocol for Characterizing the Streptavidin:Nanoparticles (SA:NPs) Ratio i. Assay of SA by the BCA method Principle In an alkaline medium, proteins reduce $Cu^{2+}$ to Cu. The salt of bicinchoninic acid (BCA) forms a colored complex with $Cu^{2+}$ ions. This complex can be quantified by its absorption at 562 nm.

Procedure

BCA assay kit from ThermoFisher (Pierce™ BCA Protein Assay Kit Cat. Num. 23225)

Preparation of the $Cu^{2+}$/BCA test reagent according to the protocol in the ThermoFisher kit.

Preparation of the SA for the standard curve. For the calibration curve, the assay is carried out three times.

TABLE 2

| streptavidin concentration of the standard solutions | |
|---|---|
| Tubes | Final SA concentration (μg/mL) |
| A | 2000 |
| B | 1500 |
| C | 1000 |
| D | 750 |
| E | 500 |
| F | 250 |
| G | 125 |
| H | 25 |
| I | 0 = white |

The procedure is as follows:

Take a 96-well plate. Place 25 μL of each standard tube A to I (with a known concentration of SA) or of nanoparticle-conjugated proteins for assay in the corresponding wells.

Add 200 μL of the $Cu^{2+}$/BCA test reagent to each well. Homogenize, cover, and incubate at 37° C. for 30 min.

Read off the absorbances (A) at 562 nm as a function of the final concentration, taking account of the dilution. Establish the standardization relationship A=f (concentration of SA in μg/mL) by linear regression.

The concentration of the nanoparticle-conjugated proteins for assay is deduced from the equation of the linear regression obtained with the standard curve.

ii. Characterization of the SA:NPs Ratio

The mass concentration of streptavidin as obtained with the BCA assay is converted to molar concentration via the following formula:

$$[SA]_{molar}(\text{mol/L}) = \frac{[SA]\text{mass (g/L)}}{\text{Molar mass (g/mol)}}$$

To give the ratio (R) of the number of SA:NPs, we apply, finally, the following $$R = \frac{[SA]\text{molar}}{[NPs]\text{molar}}$$

equation:

Table 3 below collates the values obtained for the various concentration ratios of the streptavidin solution to the starting nanoparticle solution.

TABLE 3

Characterization of nanoparticle-streptavidin coupling for various concentration ratios of the streptavidin solution to the nanoparticle solution.

| | 1:1 | 5:1 | 10:1 |
|---|---|---|---|
| Concentration ratios of the streptavidin solution to the nanoparticle solution | | | |
| Number of streptavidin molecules determined per nanoparticle at the end of coupling | 0.97 | 3.8 | 9.29 |

As is apparent from the results presented in table 3, the number of molecules of streptavidin per nanoparticle after coupling is of the same order as the concentration ratio in the initial solutions, and thus indicates highly effective coupling.

The nanoparticles coupled in this way to the streptavidin may be used advantageously in an in vitro diagnostic technique, by coupling the nanoparticles to a biotinylated antibody, as illustrated schematically in FIG. 6.

Alternatively, it is also possible for antibodies to be coupled directly to the nanoparticles grafted with citrate ions. In that case, the same protocol as above should be used, with the streptavidin solution replaced with a solution of antibody.

Example 5 (Not Inventive)

Synthesis of $Y_{0.6}Eu_{0.4}VO_4$ Nanoparticles from Sodium Metavanadate, with Addition of Tetraalkylammonium Ions at the End of Synthesis A colloidal suspension of $Y_{0.6}Eu_{0.4}VO_4$ nanoparticles is prepared from sodium salts, in accordance with the synthesis of example 2.

Purification is carried out by dialysis.

One equivalent (relative to the vanadate ions) of tetramethylammonium hydroxide $N(CH_3)_4OH$ is added, the suspension is left for 20 minutes, and it is then dialyzed again to remove the excess counterions until the resulting conductivity is strictly less than 100 μS·cm$^{-1}$.

The zeta potential, determined as described in example 1, at the resulting suspension pH of 8.9 is −2.20 mV.

It is not possible to obtain the same result as with the method of the invention using a standard method of nanoparticle synthesis and then, at the end of the synthesis, adding bulky tetraalkylammonium ions.

REFERENCES

[1] "Bioconjugate Techniques", G T Hermanson, Academic Press, 1996;
[2] "Fluorescent and Luminescent Probes for Biological Activity. A Practical Guide to Technology for Quantitative Real-Time Analysis", Second Edition, Mason W T, Ed., Academic Press, 1999;
[3] Nam et al., Science 301, 1884-1886 (2003);
[4] Riwotzki et al., J. Phys. Chem. B 1998, 105, 12709-127;
[5] Huignard et al., Chem. Mater. 2000, 12, 1090-1094;
[6] Riwotzki et al., Angew. Chem. 2001, 40(3), 573-576;
[7] Lehmann et al., J. Am. Chem. Soc. 2004, 126(45), 14935-14942;
[8] Riwotzki et al., J. Phys. Chem. B.I, IB, 2000, 104, 2824-2828;
[9] Huignard et al., Chem. Mater. 2000, 12, 10920-1094;
[10] Giaume et al., Langmuir 2008, 24, 11018-11026;
[11] Huignard et al., Chem. Mater. 2002, 14, 2264-2269;
[12] Riwotzki et al., J. Phys. Chem. B 1998, 102, 10129-10135;
[13] Mialon et al., Acs Nano, 2008-ACS Publication, vol. 2, No. 12, 2505-2512;
[14] Li et al., J. Phys. Chem. C 2008, 112, 6228-6231;
[15] Wu et al., J. Mater. Chem., 2003, 13, 1223-1228;
[16] Liang et al., J. Alloys and Compounds 552 (2013) 289-293;
[17] Wu et al., J. Phys. Chem. B 2006, 110, 15791-15796;
[18] Xu et al., Inorg. Chem. 2010, 49, 6706-6715;
[19] Takeshita et al., Journal of Luminescence 128 (2008) 1515-1522.

The invention claimed is:

1. A luminescent particle comprising a nanoparticle of formula:

$$A_{1-x}Ln_xVO_{4(1-y)}(PO_4)_y \quad (I)$$

in which:
A is selected from yttrium (Y), gadolinium (Gd), lanthanum (La), and mixtures thereof;
Ln is selected from europium (Eu), dysprosium (Dy), samarium (Sm), neodymium (Nd), erbium (Er), ytterbium (Yb), and mixtures thereof;
$0<x<1$; and
$0\leq y<1$;
wherein the nanoparticle has, at the surface, tetraalkylammonium cations in an amount such that said nanoparticle has a zeta potential, $\zeta$, of less than or equal to $-28$ mV in an aqueous medium with a pH≥5, and with an ionic conductivity of strictly less than 100 μS·cm$^{-1}$.

2. The particle as claimed in claim 1, wherein said tetraalkylammonium cations are associated with the nanoparticle via electrostatic interactions with the negatively charged O$^{2-}$ surface ions of the nanoparticle.

3. The particle as claimed in claim 1, wherein said tetraalkylammonium cations are cations of formula NR$_4^+$ where R, which are identical or different, represent a C$_1$-C$_6$-alkyl.

4. The particle as claimed in claim 1, wherein said tetraalkylammonium cations are selected from tetramethylammonium, tetraethylammonium, tetrapropylammonium, tetrabutylammonium, and mixtures thereof.

5. The particle as claimed in claim 1, wherein said nanoparticle has a zeta potential $\zeta$ of less than or equal to $-30$ mV in an aqueous medium with a pH≥6.5, and with an ionic conductivity of strictly less than 100 μS·cm$^{-1}$.

6. The particle as claimed in claim 1, said nanoparticle being of formula (I')

$$A_{1-x}Ln_xVO_{4(1-y)}(PO_4)_y \cdot (NR_4^+)_z \quad (I')$$

in which:
A is selected from Y, Gd, La, and mixtures thereof;
Ln is selected from Eu, Dy, Sm, Nd, Er, Yb, and mixtures thereof;
$0<x<1$;
$0\leq y<1$;
R, which are identical or different, represent a C$_1$-C$_6$-alkyl; and
z represents the number of tetraalkylammonium cations NR$_4^+$ located on the surface of said nanoparticle.

7. The particle as claimed in claim 1, wherein y is 0.

8. The particle as claimed in claim 1, wherein A represents Y.

9. The particle as claimed in claim 1, wherein Ln represents Eu.

10. The particle as claimed in claim 1, wherein said nanoparticle is of formula $Y_{1-x}Eu_xVO_4 \cdot (NR_4^+)_z$ (III'), in which:
$0<x<1$;
R, which are identical or different, represent a C$_1$-C$_6$-alkyl
z represents the number of tetraalkylammonium cations NR$_4^+$ located on the surface of said nanoparticle.

11. The particle as claimed in claim 1, wherein the nanoparticle of formula (I) has an elongated ellipsoidal shape.

12. The particle as claimed in claim 1, wherein the product of the degree of doping, x, with Ln ions, and the quantum yield of the emission by the nanoparticle is maximized.

13. The particle as claimed in claim 1, wherein said nanoparticle is coupled to at least one targeting agent.

14. A method for preparing luminescent particles comprising a nanoparticle of formula:

$$A_{1-x}Ln_xVO_{4(1-y)}(PO_4)_y \quad (I)$$

in which:
A is selected from yttrium (Y), gadolinium (Gd), lanthanum (La), and mixtures thereof;
Ln is selected from europium (Eu), dysprosium (Dy), samarium (Sm), neodymium (Nd), erbium (Er), ytterbium (Yb), and mixtures thereof;
$0<x<1$; and
$0\leq y<1$;
by coprecipitation reaction, in aqueous medium, from precursors of said elements A and Ln, and in the presence of orthovanadate (VO$_4^{3-}$) and optionally phosphate (PO$_4^{3-}$) ions;
said reaction being performed in the presence of an effective amount of tetraalkylammonium cations such that said nanoparticle has a zeta potential, $\zeta$, of less than or equal to $-28$ mV in an aqueous medium with a pH≥5, and with an ionic conductivity of strictly less than 100 μS·cm$^{-1}$.

15. The method as claimed in claim 14, said method comprising at least the steps of:
(i) providing an aqueous solution, called solution (1), comprising orthovanadate ions (VO$_4^{3-}$), and optionally phosphate ions (PO$_4^{3-}$), and tetraalkylammonium cations;

(ii) admixing the aqueous solution (1) with an aqueous solution, called solution (2), comprising said precursors of the elements A and Ln, under conditions conducive to the formation by coprecipitation of the nanoparticles of formula (I); and (iii) recovering the nanoparticles of formula (I) with tetraalkylammonium cations located on their surface that are formed at the end of step (ii).

16. The method as claimed in claim 14, wherein the tetraalkylammonium cations are selected from tetramethylammonium, tetraethylammonium, tetrapropylammonium, tetrabutylammonium, and mixtures thereof.

17. The method as claimed in claim 14 for preparing particles of formula (I')

(I')

in which:

A is selected from Y, Gd, La, and mixtures thereof;

Ln is selected from Eu, Dy, Sm, Nd, Er, Yb, and mixtures thereof;

$0<x<1$;

$0\leq y<1$;

R, which are identical or different, represent a $C_1$-$C_6$-alkyl; and z represents the number of tetraalkylammonium cations $NR_4^+$ located on the surface of said nanoparticle.

18. The method as claimed in claim 14, wherein the orthovanadate ions ($VO_4^{3-}$) are generated in situ by reacting a metavanadate salt, with a base.

19. The method as claimed in claim 14, said method further comprising one or more steps of coupling the particles with one or more targeting agents.

20. A colloidal aqueous suspension comprising particles as defined in claim 1.

21. A method of diagnostics, comprising:

coupling the luminescent particles as defined in claim 1 to one or more targeting agents of a substance of biological or chemical interest to obtain a diagnostic probe;

implementing said diagnostic probe in an in vitro, ex vivo, or in vivo diagnostic technique; and detecting and/or quantifying said substance of biological or chemical interest.

22. A diagnostic kit comprising at least particles as defined in claim 1, or a colloidal aqueous suspension of these particles.

23. The particle as claimed in claim 6, wherein z is between 100 and 10,000.

24. A colloidal aqueous suspension comprising particles obtained by the method defined in claim 14.

25. A method of diagnostics, comprising:

coupling the luminescent particles obtained by the method of claim 14 to one or more targeting agents of a substance of biological or chemical interest to obtain a diagnostic probe;

implementing said diagnostic probe in an in vitro, ex vivo, or in vivo diagnostic technique; and detecting and/or quantifying said substance of biological or chemical interest.

26. A diagnostic kit comprising at least particles obtained by the method defined in claim 14, or a colloidal aqueous suspension of these particles.

* * * * *